(12) United States Patent  
Kokubo (10) Patent No.: US 9,053,912 B2  
(45) Date of Patent: Jun. 9, 2015

(54) FINE PARTICLE MEASUREMENT SYSTEM

(71) Applicant: NGK SPARK PLUG CO., LTD., Nagoya-shi, Aichi (JP)

(72) Inventor: Kazunari Kokubo, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 0 days.

(21) Appl. No.: 14/266,982

(22) Filed: May 1, 2014

(65) Prior Publication Data

US 2014/0326873 A1    Nov. 6, 2014

(30) Foreign Application Priority Data

May 2, 2013    (JP) .................................. 2013-096702

(51) Int. Cl.
*H01J 49/00*    (2006.01)
*H01J 49/02*    (2006.01)

(52) U.S. Cl.
CPC .................................. *H01J 49/022* (2013.01)

(58) Field of Classification Search
USPC .................................. 250/281, 282, 283, 288
See application file for complete search history.

(56) References Cited

U.S. PATENT DOCUMENTS

2012/0234172 A1    9/2012    Sugiyama et al.
2012/0262182 A1*   10/2012   Matsuoka et al. ............ 324/464

FOREIGN PATENT DOCUMENTS

JP    2012-194078 A    10/2012
JP    2012-220423 A    11/2012

* cited by examiner

*Primary Examiner* — Nicole Ippolito
(74) *Attorney, Agent, or Firm* — Sughrue Mion, PLLC (57) ABSTRACT

A fine particle measurement system including a primary-side power supply circuit connected to a primary side of an isolation transformer, a control circuit configured to control the primary-side power supply circuit, a first current measurement circuit configured to transmit to the control circuit a first signal indicating a first current that flows from a trapping unit toward a secondary-side reference potential line, and a second current measurement circuit configured to transmit to the control circuit a second signal indicating a second current corresponding to the amount of ions that are not trapped by the trapping unit. The control circuit adjusts the electrical power supplied to the ion generating unit based on the first current and measures the amount of the fine particles in the gas based on the second current. Further, the first current measurement circuit includes an isolation amplifier and amplifies the first signal via the isolation amplifier and transmits the first signal to the control circuit.

2 Claims, 4 Drawing Sheets

FINE PARTICLE MEASUREMENT SYSTEM

BACKGROUND OF THE INVENTION

1. Field of the Invention

The present invention relates to a fine particle measurement system for measuring the amount of fine particles such as soot contained in a gas.

2. Description of the Related Art

Conventionally, a fine particle measurement system is known for measuring the amount of fine particles such as soot contained in exhaust gas from an internal combustion engine such as a diesel engine. This fine particle measurement system generates ions by corona discharge to electrically charge the fine particles in the exhaust gas by the ions thus generated, traps the ions that are not used for electrically charging the fine particles, and based on the trapped ion amount (or based on the amount of the ions used to electrically charge the fine particles, and that are not trapped), and measures the amount of the fine particles in the exhaust gas. The amount of the trapped ions correlates with the amount of the ions used for electrically charging, while the amount of the ions used for electrically charging correlates to the amount of the fine particles in the exhaust gas, so that this fine particle measurement system is capable of measuring the amount of the fine particles in the exhaust gas based on the amount of the trapped ions.

Concerning this fine particle measurement system, known in the art is an ion-source power supply circuit for generating ions, a source power supply circuit casing that surrounds the ion-source power supply circuit, and a signal current detection circuit for detecting a signal current which correlates to the amount of trapped ions. These components are electromagnetically shielded by a surrounding outer circuit casing (Patent Literature 1). In addition, by using a separation electrode for generating a repulsive force on ions that are not used for electrically charging fine particles, and the separation electrode is disposed so as to pass through a nozzle component member including a nozzle for injecting the ions, where the separation electrode and the nozzle component member are insulated by a ceramic member (Patent Literature 2).

[Patent Literature 1] JP-A-2012-220423
[Patent Literature 2] JP-A-2012-194078

3. Problems to be Solved by the Invention

However, as for the fine particle measurement systems disclosed in the above-described related art, there is still room for improvement in terms of accuracy in detecting the amount of fine particles in exhaust gas. In general, the current corresponding to the amount of ions that are used for electrically charging the fine particles is very small, which makes it difficult to detect a current value with accuracy. For example, an unintended slight current (leakage current) occasionally flows in a circuit of the fine particle measurement system. This results from deteriorated insulation performance and the like, which might be caused by an applied high voltage for discharge purposes or humidity of an insulation members used for the fine particle measurement system. When the leakage current is generated, an error occurs in a current value that is detected as the current corresponding to the amount of ions that are used for electrically charging the fine particles.

On conceivable example of the fine particle measurement system is a fine particle measurement system that includes a power supply circuit on a primary side of an isolation transformer, an ion generating unit and an ion trapping unit on a secondary side of the isolation transformer, and a current measurement circuit that is disposed between the primary side and the secondary side. The current measurement circuit supplies the secondary side with a current corresponding to the amount of ions that are used for electrically charging the fine particles as a compensating current, and detects the current value of the compensating current. With this configuration, it is possible to detect the amount of the fine particles in exhaust gas based on the current value of the compensating current detected by the current measurement circuit. However, in this fine particle measurement system, when a leakage current runs from the primary side to the secondary side in an area other than the current measurement circuit, an error occurs between the current value of the compensating current and the current value of the current corresponding to the amount of ions that are used for electrically charging the fine particles. A problem thereby arises in that the amount of the fine particles in exhaust gas cannot be detected with accuracy.

SUMMARY OF THE INVENTION

The present invention was made in order to solve the above problems of the related art. It is therefore an object of the present invention to provide a fine particle measurement system having increased accuracy in detecting the amount of fine particles contained in an exhaust gas.

The above object of the present invention has been achieved by providing (1) a fine particle measurement system comprising: an ion generating unit configured to generate ions by corona discharge, and a charging chamber configured to charge at least a part of fine particles present in a gas with said ions; a trapping unit in communication with the charging chamber, and configured to trap at least a part of the generated ions that do not electrically charge the fine particles; an isolation transformer configured to transform a voltage used for generating the corona discharge, the isolation transformer comprising a secondary side connected to the ion generating unit; a primary-side power supply circuit connected to a primary side of the isolation transformer, and capable of changing a voltage supplied to the isolation transformer; a control circuit connected to the primary-side power supply circuit, and configured to control the primary-side power supply circuit so as to adjust a current supplied to the ion generating unit; a first current measurement circuit connected to each of a secondary-side reference potential line of a secondary side of the isolation transformer, the trapping unit and the control circuit, and configured to transmit to the control circuit a first signal indicating a first current that flows from the trapping unit toward the secondary-side reference potential line; and a second current measurement circuit connected to each of a primary-side reference potential line of a primary side of the isolation transformer, the secondary-side reference potential line and the control circuit, and configured to transmit to the control circuit a second signal indicating a second current that is obtained based on a potential difference between the primary-side reference potential line and the secondary-side reference potential line, the second current corresponding to an amount of ions that are not trapped by the trapping unit, wherein the control circuit is configured to adjust the current supplied to the ion generating unit to a desired value in accordance with the first current, and to measure the amount of the fine particles in the gas in accordance with the second current, and wherein the first current measurement circuit comprises an isolation amplifier and is configured to amplify the first signal via the isolation amplifier to transmit the first signal to the control circuit.

In this configuration, there are two current measurement circuits, each connected to a primary-side circuit and a secondary-side circuit (the first current measurement circuit and the second current measurement circuit). The first current measurement circuit constituting a constant current circuit includes an isolation amplifier that is physically isolated between the primary side and the secondary side (specifically, between the primary side corresponding to an input unit and the secondary side corresponding to an output unit) in like manner of the isolation transformer. Therefore, the present fine particle measurement system is configured such that only the second current measurement circuit electrically connects the primary-side circuit and the secondary-side circuit, which configuration can prevent the generation of a leakage current from the primary side to the secondary side in any area except the second current measurement circuit. Preventing the generation of a leakage current in areas other than the second current measurement circuit can reduce an error between a compensating current supplied to the secondary side and a current corresponding to the amount of ions used for electrically charging the fine particles in the second current measurement circuit. In addition, since the control circuit is configured to adjust the current supplied to the ion generating unit to a desired current based on the first signal amplified by the isolation amplifier, it is possible to control the current with more accuracy. Therefore, according to the present fine particle measurement system, it is possible to increase the accuracy in detecting the amount of the fine particles contained in the gas.

In a preferred embodiment (2) of the fine particle measurement system according to (1) above, the gas comprises an exhaust gas exhausted from an internal combustion engine, and the charging chamber is disposed in an exhaust pipe through which the exhaust gas passes.

In this configuration, it is possible to increase the accuracy in detecting the amount of the fine particles contained in the exhaust gas exhausted from the internal combustion engine, so that using the detected amount of the fine particles can increase detection accuracy of a broken condition of a filter for trapping fine particles in the exhaust gas, or increase the reliability of accuracy of a variety of controls of the internal combustion engine.

The present invention can be achieved in a variety of forms. For example, the present invention can be achieved in the form of a fine particle sensor, a fine particle detection method, an internal combustion engine including a fine particle measurement system, a vehicle including the internal combustion engine, and the like.

DESCRIPTION OF REFERENCE NUMERALS

Reference numerals used to identify various structural features in the drawings include the following.
10 Fine particle measurement system
25 Ceramic pipe
31 Gas flow passage
35 Outflow hole
41 Nozzle
42 Partition wall
45 Inflow hole
55 Air supply hole
100 Fine particle sensor
110 Ion generation unit
111 Ion generation chamber
112 First electrode
120 Exhaust gas charging unit
121 Charging chamber
130 Ion trapping unit
131 Trapping chamber
132 Second electrode
200 Cable
221 First line
222 Second line
223 Signal line
224 Air supply pipe
230 Shunt resistance
300 Sensor driving unit
400 Internal combustion engine
402 Exhaust gas pipe
405 Fuel pipe
410 Filtering device
420 Vehicle control unit
430 Fuel supply unit
440 Power supply unit
500 Vehicle
600 Sensor control unit
700 Electric circuit unit
710 Primary-side power supply circuit
711 Discharge voltage control circuit
712 Transformer driving circuit
720 Insulation transformer
730 Corona current measurement circuit
731 First operational amplifier
733 Light emitting unit
734 Light receiving unit
735 Second operational amplifier
740 Ion current measurement circuit
741 Operational amplifier
742 Resistor
743 Line
751 First rectification circuit
752 Second rectification circuit
753 Short-circuit protecting resistor
754 Short-circuit protecting resistor
761 to 763 Lines
771 to 773 Lines
800 Air supply unit

DETAILED DESCRIPTION OF THE PREFERRED EMBODIMENTS

The invention will not be described in greater detail by reference to the drawings. However, the present invention should not be construed as being limited thereto.

A. First Embodiment

Figure 1A:
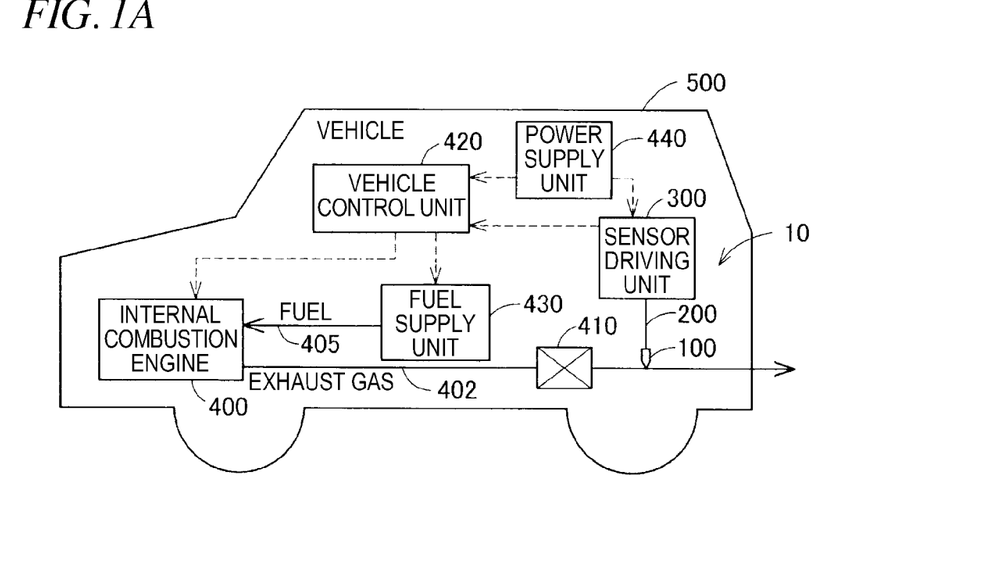
FIGS. 1A and 1B are explanatory views illustrating an overall configuration of a fine particle measurement system according to a first embodiment of the invention.
Figure 1B:
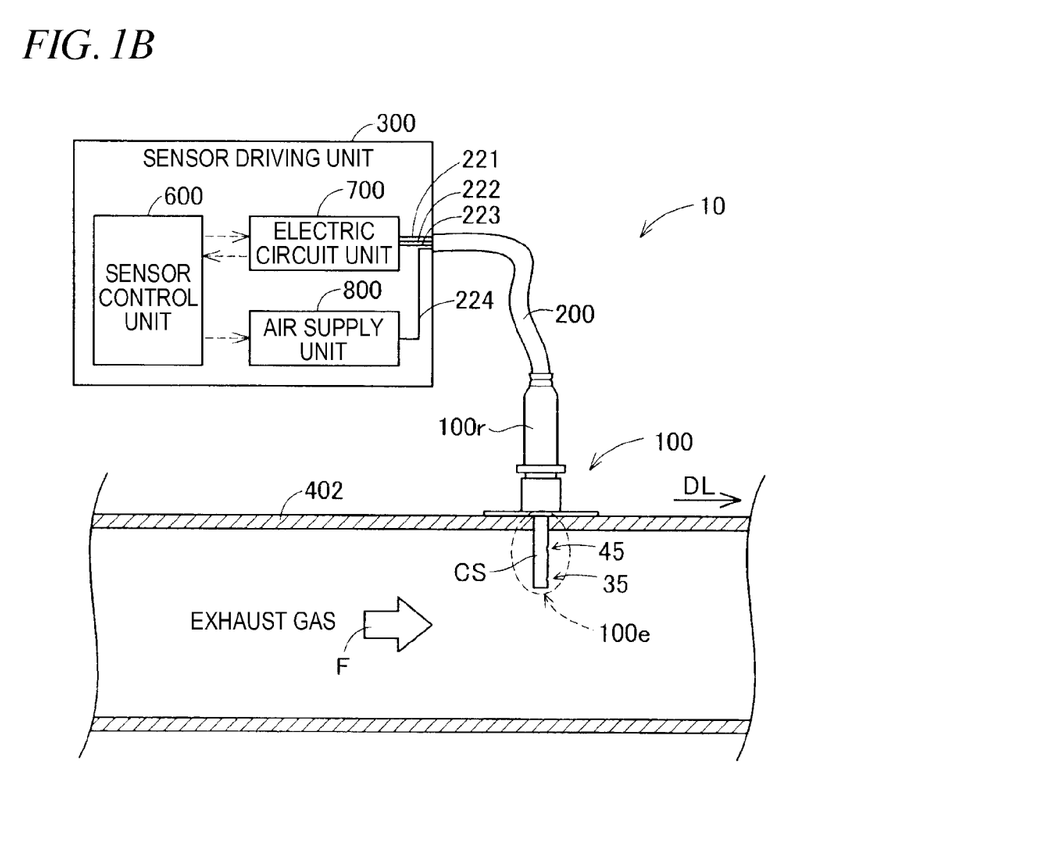

A. First embodiment: FIGS. 1A and 1B are explanatory views illustrating an overall configuration of a fine particle measurement system 10 according to a first embodiment of the present invention. FIG. 1A is an explanatory view showing a block diagram of a vehicle 500 including a fine particle measurement system 10. FIG. 1B is an explanatory view showing a block diagram of the fine particle measurement system 10 installed in the vehicle 500. The fine particle measurement system 10 includes a fine particle sensor 100, a cable 200 and a sensor driving unit 300, and is configured to measure the amount of fine particles such as soot contained in exhaust gas exhausted from an internal combustion engine 400. The internal combustion engine 400 defines a power source of the vehicle 500, and includes a diesel engine and the like.

The fine particle sensor 100 is attached to an exhaust gas pipe 402 extending from the internal combustion engine 400, and is electrically connected to the sensor driving unit 300 by the cable 200. In the present embodiment, the fine particle sensor 100 is attached to the exhaust gas pipe 402 located on the downstream side of a filtering device 410 (e.g., a DPF (Diesel Particulate Filter)). The fine particle sensor 100 outputs a signal which correlates with the amount of the fine particles contained in the exhaust gas to the sensor driving unit 300.

The sensor driving unit 300 drives the fine particle sensor 100, and detects the amount of the fine particles contained in the exhaust gas based on the signal inputted from the fine particle sensor 100. The amount of the fine particles contained in the exhaust gas that the sensor driving unit 300 detects may be a value proportional to the sum total of surface areas of the fine particles contained in the exhaust gas, or may be a value proportional to the sum total of weights of the fine particles contained in the exhaust gas. Alternatively, this may be proportional to the number of the fine particles in a unit volume of the exhaust gas. The sensor driving unit 300 is electrically connected to a vehicle control unit 420 on the side of the vehicle 500, and outputs a signal, indicating the detected amount of the fine particles contained in the exhaust gas, to the vehicle control unit 420. In accordance with the signal inputted from the sensor driving unit 300, the vehicle control unit 420 controls a combustion state of the internal combustion engine 400, an amount of fuel supplied to the internal combustion engine 400 from a fuel supply unit 430 via a fuel pipe 405, and the like. The vehicle control unit 420 may be, for example, configured to alert a driver of the vehicle 500 to deterioration or an abnormality of the filtering device 410 in case the amount of the fine particles contained in the exhaust gas is larger than a predetermined amount. Each of the sensor driving unit 300 and the vehicle control unit 420 is electrically connected to a power supply unit 440, and supplied with electrical power from the power supply unit 440.

As shown in FIG. 1B, the fine particle sensor 100 includes a tip end portion 100e having a cylindrical shape, and is fixed to the outer surface of the exhaust gas pipe 402 with the tip end portion 100e inserted inside of the exhaust gas pipe 402. In FIG. 1B, the tip end portion 100e of the fine particle sensor 100 is inserted approximately vertically to a drawing direction DL of the exhaust gas pipe 402. An inflow hole 45 for taking in exhaust gas into a casing CS and an outflow hole 35 for exhausting the exhaust gas are provided on the surface of the casing CS of the tip end portion 100e. A part of the exhaust gas that flows through inside of the exhaust gas pipe 402 is taken into the casing CS of the tip end portion 100e via the inflow hole 45. The fine particles contained in the exhaust gas that has been taken in are electrically charged by ions (in the present embodiment, cations) generated in the fine particle sensor 100. The exhaust gas containing the electrically-charged fine particles is discharged outside of the casing CS via the outflow hole 35. The configuration inside of the casing CS and the specific configuration of the fine particle sensor 100 are described below.

The cable 200 is attached to a rear end portion 100r of the fine particle sensor 100. The cable 200 includes a first line 221, a second line 222, a signal line 223 and an air supply pipe 224 that are tied in a bundle. The lines 221 to 223 and the pipe 224 that constitute the cable 200 are each flexible members. The first line 221, the second line 222 and the signal line 223 are electrically connected to the sensor driving unit 300, and the air supply pipe 224 is connected to an air supply unit 800.

The sensor driving unit 300 includes a sensor control unit 600, an electric circuit unit 700 and the air supply unit 800. The sensor control unit 600 and the electric circuit unit 700 are electrically connected to each other, and the sensor control unit 600 and the air supply unit 800 are electrically connected to each other.

The sensor control unit 600 includes a microcomputer, and controls the electric circuit unit 700 and the air supply unit 800. In addition, the sensor control unit 600 detects the amount of the fine particles contained in the exhaust gas based on a signal inputted from the electric circuit unit 700, and outputs a signal indicating the amount of the fine particles contained in the exhaust gas to the vehicle control unit 420.

The electric circuit unit 700 supplies electric power to drive the fine particle sensor 100 via the first line 221 and the second line 222. In addition, the signal which correlates with the amount of the fine particles contained in the exhaust gas is inputted to the electric circuit unit 700 from the fine particle sensor 100 via the signal line 223. The electric circuit unit 700 outputs the signal which correlates with the amount of the fine particles contained in the exhaust gas to the sensor control unit 600 based on the signal inputted from the signal line 223. Specific descriptions of these signals are given below.

The air supply unit 800 includes a pump (not illustrated), and supplies high-pressure air to the fine particle sensor 100 via the air supply pipe 224 based on an instruction from the sensor control unit 600. The high-pressure air supplied from the air supply unit 800 is used to drive the fine particle sensor 100. The gas supplied by the air supply unit 800 may be a gas other than air.

Figure 2:
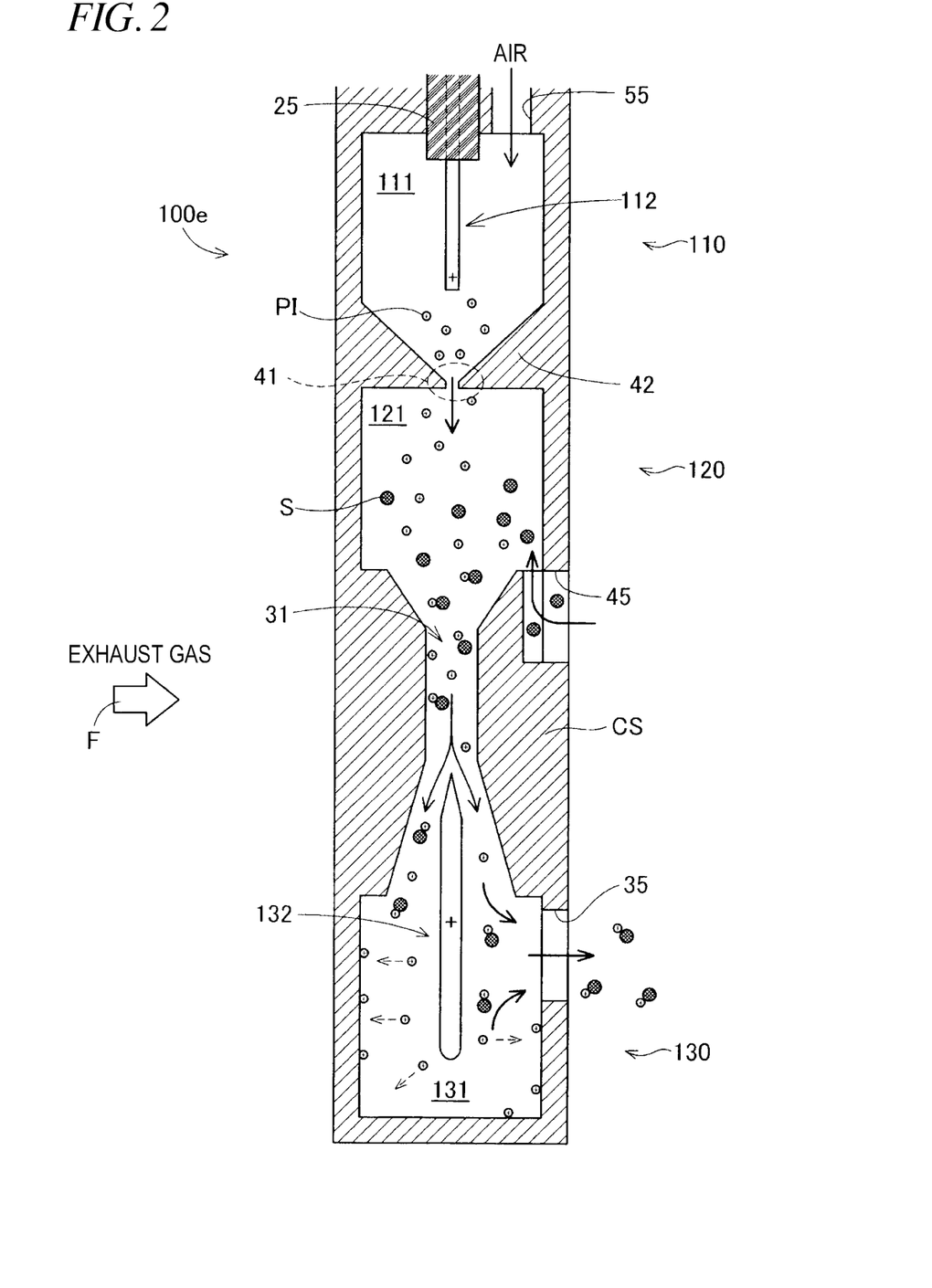
FIG. 2 is an explanatory view schematically showing a schematic configuration of a tip end portion of a fine particle sensor.

FIG. 2 is an explanatory view schematically showing a schematic configuration of the tip end portion 100e of the fine particle sensor 100. The tip end portion 100e of the fine particle sensor 100 includes an ion generation unit 110, an exhaust gas charging unit 120 and an ion trapping unit 130. The casing CS is configured such that three mechanical sections of the ion generation unit 110, the exhaust gas charging unit 120 and the ion trapping unit 130 are arranged in order from the base end side (shown in the upper portion of FIG. 2) to the tip end side (as shown in the bottom portion of FIG. 2) of the tip end portion 100e (in other words, along the direction of the axial line of the fine particle sensor 100). The casing CS is made of a conductive member, and is connected to a secondary side ground SGL (FIG. 3) via the signal line 223 (FIG. 1).

The ion generation unit 110 defines a mechanical section for generating ions (in the present embodiment, cations) supplied to the exhaust gas charging unit 120, and includes an ion generation chamber 111 and a first electrode 112. The ion generation chamber 111 defines a small empty space formed inside of the casing CS, and includes an air supply hole 55 and a nozzle 41 on its inner periphery. The first electrode 112 is attached to the inside of the ion generation chamber 11 so as to protrude therefrom. The air supply hole 55 communicates with the air supply pipe 224 (FIG. 1), and supplies the high-pressure air supplied from the air supply unit 800 (FIG. 1) to the ion generation chamber 111. The nozzle 41 defines a very tiny hole (orifice) provided close to the center of a partition wall 42 that partitions the ion generation chamber 111 and the exhaust gas charging unit 120, and supplies the ions generated in the ion generation chamber 111 to a charging chamber 121 of the exhaust gas charging unit 120. The first electrode 112 has an outer shape of a rod. A base end portion of the first electrode 112 is fixed to the casing CS via a ceramic pipe 25 while the tip end portion is disposed close to the partition wall 42. The first electrode 112 is connected to the electric circuit unit 700 (FIG. 1) via the first line 221 (FIG. 1).

The ion generation unit 110 applies a direct-current voltage (e.g., 2 to 3 kV) to the first electrode 112 (which functions as an anode) and to the partition wall 42 (which functions as a cathode) using electric power supplied from the electric circuit unit 700. By application of this voltage, the ion generation unit 110 generates a corona discharge between the tip end portion of the first electrode 112 and the partition wall 42, to thereby generate cations PI. The cations PI generated in the ion generation unit 110 are injected into the charging chamber 121 of the exhaust gas charging unit 120 via the nozzle 41 together with the high-pressure air supplied from the air supply unit 800 (FIG. 1). The injection speed of the air injected from the nozzle 41 is preferably set to the same level as sonic speed.

The exhaust gas charging unit 120 is configured to electrically charge the fine particles contained in the exhaust gas with the cations PI, and includes the charging chamber 121. The charging chamber 121 is defined by a small empty space adjacent to the ion generation chamber 111, and is in communication with the ion generation chamber 111 via the nozzle 41. In addition, the charging chamber 121 is in communication with the outside of the casing CS via the inflow hole 45, and is in communication with a trapping chamber 131 of the ion trapping unit 130 via a gas flow passage 31. The charging chamber 121 is configured such that when air containing the cations PI is injected from the nozzle 41, the interior is placed under a negative pressure to let the exhaust gas outside of the casing CS flow into the charging chamber 121 via the inflow hole 45. Thus, air containing the cations PI injected from the nozzle 41 and the exhaust gas flowing in from the inflow hole 45 are mixed inside of the charging chamber 121. At this time, at least a part of soot S (fine particles) contained in the exhaust gas flowing in from the inflow hole 45 is electrically charged by the cations PI supplied from the nozzle 41. The air containing the soot S and the generated cations PI that are not used for electrically charging the soot S are fed to the trapping chamber 131 of the ion trapping unit 130 via the gas flow passage 31.

The ion trapping unit 130 is configured to electrically trap the generated ions that are not used for electrically charging the soot S (fine particles), and includes the trapping chamber 131 and a second electrode 132. The trapping chamber 131 defines a small empty space adjacent to the charging chamber 121, and is in communication with the charging chamber 121 via the gas flow passage 31. In addition, the trapping chamber 131 is in communication with the outside of the casing CS via the outflow hole 35. The second electrode 132 has an outer shape which approximates a rod, and is fixed to the casing CS with its longitudinal axis extending along a flow direction of the air passing through the gas flow passage 31 (a drawing direction of the casing CS). The second electrode 132 is connected to the electric circuit unit 700 (FIG. 1) via the second line 222 (FIG. 1). A voltage of about 100 V is applied to the second electrode 132, and the second electrode 132 functions as an auxiliary electrode for trapping the generated cations that are not used for electrically charging the soot S. Specifically, a voltage is applied to the ion trapping unit 130 by electric power supplied from the electric circuit unit 700 while the second electrode 132 functions as an anode, and the casing CS including the charging chamber 121 and the trapping chamber 131 function as a cathode. Thus, the generated cations PI that are not used for electrically charging the soot S are repulsed by and move away from the second electrode 132 to be trapped by the trapping chamber 131 that functions as an cathode and the inner peripheral wall of the gas flow passage 31. Meanwhile, the soot S electrically charged by the cations PI is repulsed by the second electrode 132 similarly to the generated cations PI that do not charge the soot S. However, since the charged soot S is heavier than the cations PI, the soot S electrically charged by the cations PI receives a smaller repulsive force in the direction of movement than the generated cations PI that do not charge the soot S. Thus, the electrically-charged soot S is exhausted from the outflow hole 35 to the outside of the casing CS with the flow of the exhaust gas.

The fine particle sensor 100 outputs a signal indicating a change in current in accordance with the amount of the trapped cations PI in the ion trapping unit 130. The sensor control unit 600 (FIG. 1) detects the amount of the soot S contained in the exhaust gas based on the signal outputted from the fine particle sensor 100. A method for calculating the amount of the soot S contained in the exhaust gas based on the signal outputted from the fine particle sensor 100 will be described below.

Figure 3:
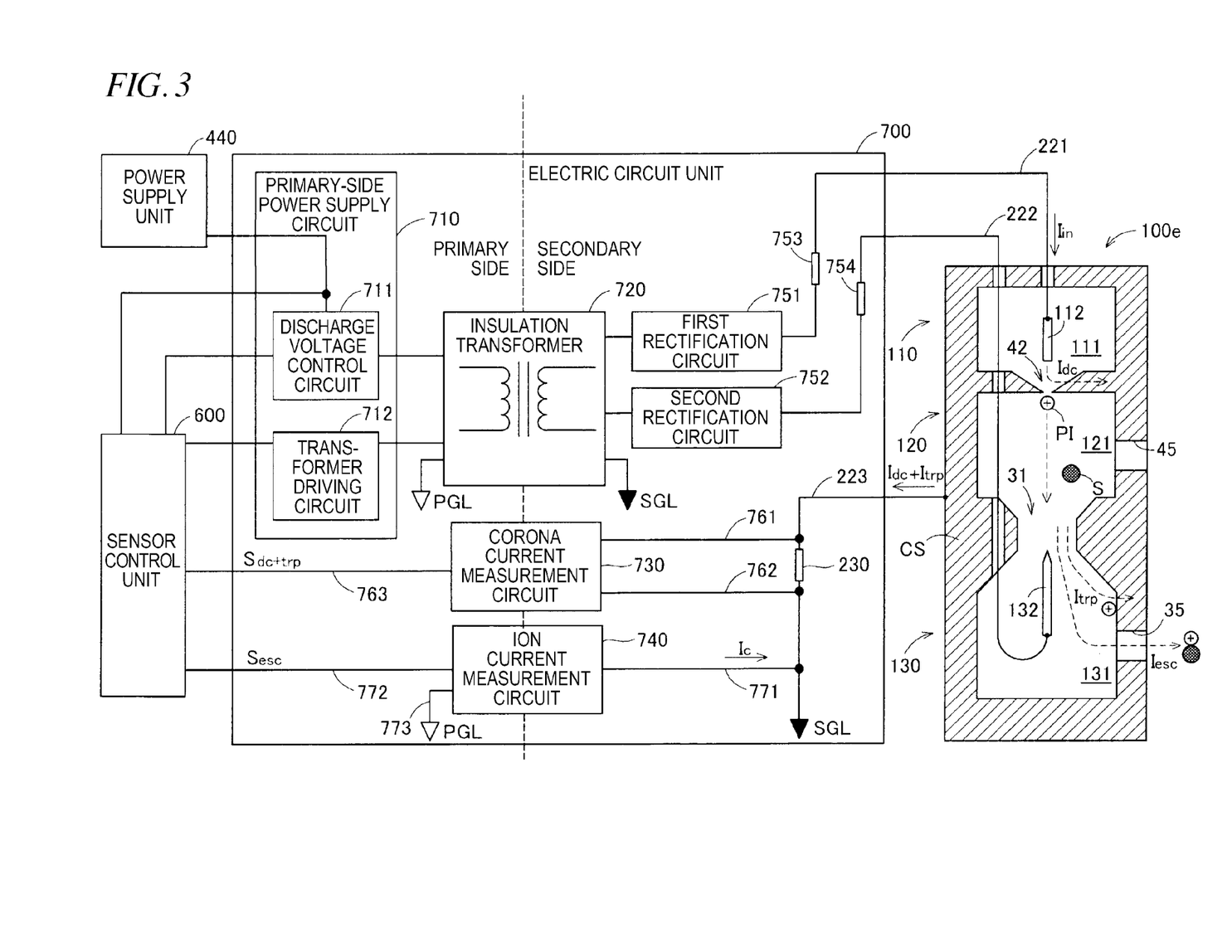
FIG. 3 is an explanatory view showing a block diagram of an electric circuit unit.

FIG. 3 is an explanatory view showing a block diagram of the electric circuit unit 700. The electric circuit unit 700 includes a primary-side power supply circuit 710, an isolation transformer 720, a corona current measurement circuit 730, an ion current measurement circuit 740, a first rectification circuit 751 and a second rectification circuit 752.

The primary-side power supply circuit 710 increases the voltage of electric power (here, direct-current power) supplied from the power supply unit 440 to drive the isolation transformer 720. The primary-side power supply circuit 710 includes a discharge voltage control circuit 711 and a transformer driving circuit 712. The discharge voltage control circuit 711 includes a DC/DC converter, and is capable of arbitrarily changing a voltage value of the electric power supplied to the insulation transformer 720 by controlling the sensor control unit 600. In this configuration, the sensor control unit 600 controls the voltage value of the electric power supplied to the isolation transformer 720 so that a current value of an input current Iin supplied to the first electrode 112 of the fine particle sensor 100 via the first line 221 assumes a desired current value (e.g., 5 µA) that is set in advance. A method of achieving this control will be described below. Thus, the amount of cations PI generated by the corona discharge can be made constant in the ion generation unit 110.

The transformer driving circuit 712 includes a switch capable of switching the direction of current flowing in a coil on the primary side of the isolation transformer 720, and drives the isolation transformer 720 by switching the current flow. In the present embodiment, a circuit system of the isolation transformer 720 is a push-pull system; however, the circuit system of the insulation transformer 720 is not limited thereto, and may be a half-bridge system, a full-bridge system, or the like.

The isolation transformer 720 transforms the voltage of the electric power supplied to the primary-side power supply circuit 710, and supplies the transformed electric power (here, an alternating-current) to the rectification circuits 751 and 752 on the secondary side. The isolation transformer 720 is capable of setting the electric power supplied to the first rectification circuit 751 so as to have a different amplifying gain than the electric power supplied to the second rectification circuit 752 by configuring a coil on the secondary side.

The isolation transformer 720 according to the present embodiment is configured such that the coils on the primary and secondary sides are not in physical contact with each other, but are magnetically connected. A primary-side circuit of the isolation transformer 720 includes the sensor control unit 600 and the power supply unit 440 in addition to the primary-side power supply circuit 710. A secondary-side circuit of the isolation transformer 720 includes the fine particle sensor 100, and the rectification circuits 751 and 752. The corona current measurement circuit 730 and the ion current measurement circuit 740 are astride the primary-side circuit and the secondary-side circuit of the isolation transformer 720, and are electrically connected to both of these circuits. The corona current measurement circuit 730 is physically isolated from a circuit portion that is electrically connected to the primary-side circuit of the isolation transformer 720, and a circuit portion that is electrically connected to the secondary-side circuit of the isolation transformer 720 as described below. A ground (ground line) which is a reference potential of the primary-side circuit is also referred to as a "primary-side ground PGL", and a ground which is a reference potential of the secondary-side circuit is referred to as a "secondary-side ground SGL". In the isolation transformer 720, an end of the coil on the primary side is connected to the primary-side ground PGL while an end of the coil on the secondary side is connected to the secondary-side ground SGL. One end of the signal line 223 is connected to the casing CS while the other end is connected to the secondary-side ground SGL.

The rectification circuits 751 and 752 rectify the alternating-current power outputted from the isolation transformer 720 while converting the alternating-current power into direct-current power. The first rectification circuit 751 is connected to the first electrode 112 via a short-circuit protecting resistor 753, and supplies the converted direct-current power to the first electrode 112 via the first line 221. In other words, the direct-current voltage supplied from the first rectification circuit 751 is approximately a discharge voltage of the first electrode 112, and the direct-current supplied from the first rectification circuit 751 is the input current Iin inputted to the first electrode 112. The second rectification circuit 752 is connected to the second electrode 132 via a short-circuit protecting resistor 754, and applies the converted direct-current power to the second electrode 132 via the second line 222.

The corona current measurement circuit 730 is configured to detect a current value of a discharge current (corona current) that flows due to the corona discharge generated in the ion generation unit 110. Further, the corona current measurement circuit 730 is connected to the signal line 223 via lines 761 and 762, and is connected to the sensor control unit 600 via a line 763. The lines 761 and 762 are connected to the signal line 223, sandwiching a shunt resistance 230 provided therebetween. The corona current measurement circuit 730 outputs to the sensor control unit 600 a signal Sdc+trp indicating a value of a current (Idc+Itrp) flowing from the casing CS to the secondary-side ground SGL via the signal line 223. The "signal indicating a current value" is not limited to signals directly indicating current values, and also corresponds to signals indirectly indicating current values. For example, signals from which current values can be specified by applying arithmetic expressions or maps to information obtained from the signals are also encompassed by the "signal indicating a current value".

As shown in Equation (1) described below, the current value of the current (Idc+Itrp) flowing through the signal line 223 is approximately equal to the current value of the input current Iin. This is because a leakage current Iesc in Equation (1) is about $1/10^6$ as large as the current (Idc+Itrp) flowing through the signal line 223, and can be substantively ignored in observing a change in the input current Iin. The current value of the input current Iin is equal to the current value of the corona current of the ion generation unit 110, so that the current value of the current (Idc+Itrp) flowing through the signal line 223 is approximately equal to the current value of the corona current. Therefore, the corona current measurement circuit 730 outputs the signal Sdc+trp indicating the current value of the corona current of the ion generation unit 110 to the sensor control unit 600. In the present embodiment, the corona current measurement circuit 730 corresponds to a "first current measurement circuit" of the invention. In addition, the current (Idc+Itrp) flowing through the signal line 223 corresponds to a "first current" of the invention. The signal Sdc+trp indicating the current value of the current flowing through the signal line 223 corresponds to a "first signal" of the invention.

The sensor control unit 600 controls the discharge voltage control circuit 711 so that the current value of the input current Iin assumes a desired current value in accordance with the signal Sdc+trp inputted from the corona current measurement circuit 730. In other words, the corona current measurement circuit 730 and the sensor control unit 600 constitute a constant current circuit for making the current value of the corona current (input current Iin) constant. The current value of the corona current correlates with the amount of cations PI generated in the ion generation unit 110, so that this constant current circuit allows the amount of cations PI generated in the ion generation unit 110 to be maintained constant.

The ion current measurement circuit 740 detects a current value of a current (Iesc) corresponding to the cations PI that are not trapped in the ion trapping unit 130 and therefore leaked to the outside while suppling the secondary-side circuit with a current (Ic) corresponding to the leaked cations PI. The ion current measurement circuit 740 is connected to the signal line 223 on the secondary side via a line 771 while connected to the sensor control unit 600 on the primary side via a wire 772. In addition, the ion current measurement circuit 740 is connected to the primary-side ground PGL via a wire 773. The ion current measurement circuit 740 outputs to the sensor control unit 600 a signal Sesc in accordance with the current value of the current corresponding to the cations PI that are not trapped in the ion trapping unit 130 and therefore leak to the outside.

A description of a method in which the ion current measurement circuit 740 detects the current value of the current corresponding to the cations PI that are not trapped in the ion trapping unit 130 and therefore leak to the outside will be given below. Hereinafter, the current supplied from the first line 221 to the first electrode 112 is referred to as an "input current Iin". The current flowing from the first electrode 112 to the casing CS via the partition wall 42 by the corona discharge is referred to as a "discharge current Idc". The current corresponding to electric charge of the cations PI that electrically charge the soot S and leak to the outside of the casing CS among the cations PI generated by the corona discharge is referred to as a "leakage current Iesc". The current corresponding to the electric charge of the cations PI that are trapped in the casing CS is referred to as a "trap current Itrp". These four currents can be expressed by following Equation (1).

$$Iin = Idc + Itrp + Iesc \quad (1)$$

Because the discharge current Idc and the trap current Itrp flow from the casing CS to the secondary-side ground SGL via the signal line 223, a total value of the discharge current Idc and the trap current Itrp can be detected from the current value of the current flowing through the signal line 223. In addition, the input current Iin is constantly controlled by the constant current circuit as described above. Accordingly, a value of the leakage current Iesc can be calculated based on the difference between the current value of the input current Iin and the current value of the current (Idc+Itrp) flowing through the signal line 223. In other words, the leakage current Iesc can be calculated by following Equation (2).

$$Iesc=Iin-(Idc+Itrp) \qquad (2)$$

Figure 4:
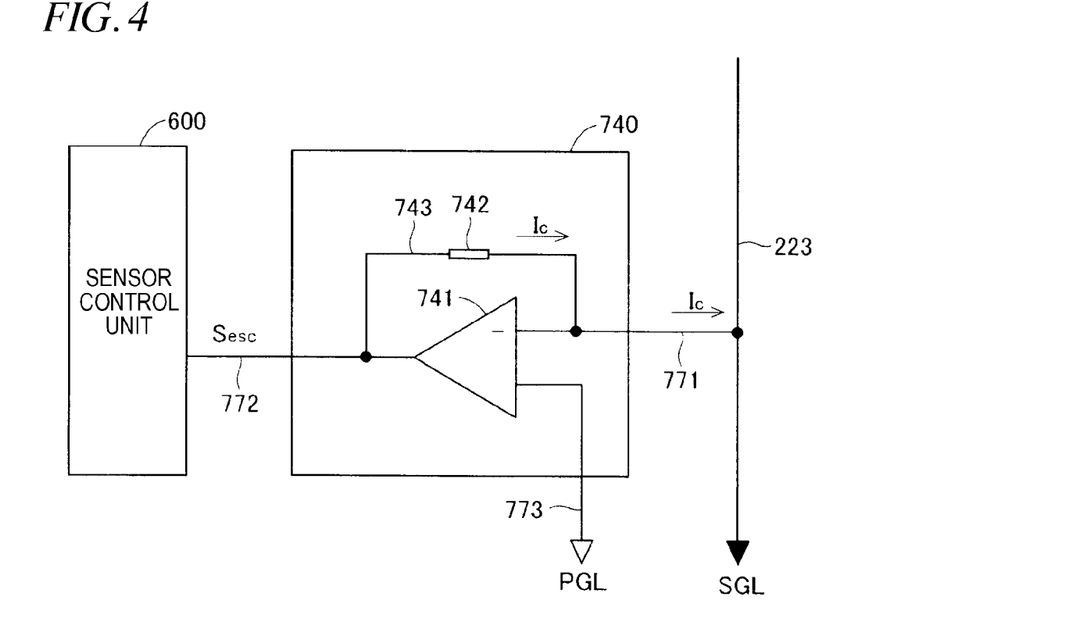
FIG. 4 is an explanatory view showing a block diagram of an ion current measurement circuit.

FIG. 4 is an explanatory view showing a block diagram of the ion current measurement circuit 740. The ion current measurement circuit 740 according to the present embodiment detects the leakage current Iesc by the following method. The ion current measurement circuit 740 includes an operational amplifier 741, a resistor 742 having a known resistance value, and a line 743 connecting the line 772 and the line 771 via the resistor 742. One input terminal of the operational amplifier 741 is connected to the secondary-side ground SGL via the line 771 and the signal line 223 while the other input terminal is connected to the primary-side ground PGL via the line 773. An output terminal of the operational amplifier 741 is connected to the sensor control unit 600 via the line 772 while connected to the line 771 via the line 743 and the resistor 742.

When the leakage current Iesc is generated, a reference potential of the secondary-side ground SGL becomes lower than a reference potential of the primary-side ground PGL depending on the magnitude of the leakage current Iesc. This is because a difference in energy (electric power) corresponding to the leakage current Iesc is developed between the energy (electric power) supplied to the fine particle sensor 100 from the primary side containing the primary-side power supply circuit 710 and the energy (electric power) outputted to the fine particle sensor 100 via the signal line 223. When a difference exists between the reference potential of the secondary-side ground SGL and the reference potential of the primary-side ground PGL by generation of the leakage current Iesc, the operational amplifier 741 outputs a voltage in accordance with the difference. The voltage outputted by the operational amplifier 741 correlates with the current value of the leakage current Iesc, so that the voltage value is outputted as a signal Sesc indicating the current value of the leakage current Iesc to the sensor control unit 600 via the line 772. In addition, the voltage outputted by the operational amplifier 741 is supplied as a compensating current Ic to the line 771 via the resistor 742. The compensating current Ic has a current value equal to the leakage current Iesc, and by being supplied to the line 771 constituting the secondary-side circuit, compensates for the difference between the reference potential of the secondary-side ground SGL and the reference potential of the primary-side ground PGL. In the present embodiment, the ion current measurement circuit 740 corresponds to a "second current measurement circuit" of the invention. In addition, the compensating current Ic corresponds to a "second current" of the invention. In addition, the signal indicating the compensating current Ic corresponds to a "second signal" of the invention.

The sensor control unit 600 detects the amount of the soot S contained in the exhaust gas from the signal Sesc indicating the current value of the leakage current Iesc that is inputted from the ion current measurement circuit 740. The method for detecting the amount of the soot S contained in the exhaust gas from the current value of the leakage current Iesc is not specifically limited. For example, if storing a map indicating a correspondence relation between the current value of the leakage current Iesc and the amount of the soot S contained in the exhaust gas, or if storing a relational expression between the current value of the leakage current Iesc and the amount of the soot S contained in the exhaust gas, then the sensor control unit 600 is capable of calculating the amount of soot S contained in the exhaust gas by using the map or the expression.

Figure 5:
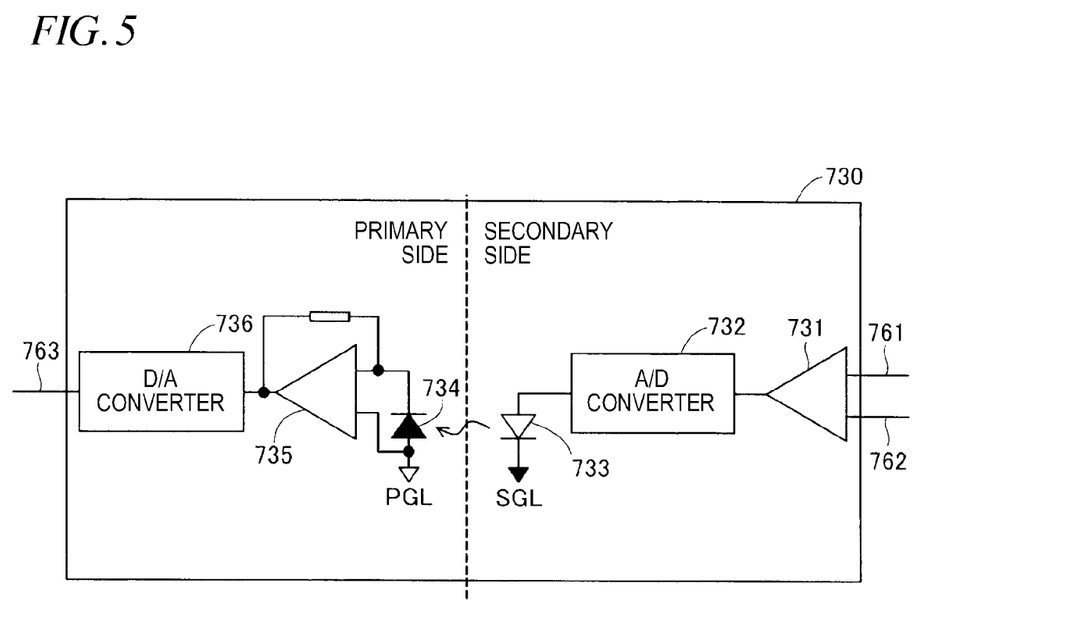
FIG. 5 is an explanatory view showing a block diagram of a corona current measurement circuit.

FIG. 5 is an explanatory view showing a block diagram of the corona current measurement circuit 730. The corona current measurement circuit 730 includes a so-called optical coupling type isolation amplifier that isolates the input side from the output side. The input side of the corona current measurement circuit 730 is associated with the secondary side of the electric circuit unit 700 (FIG. 3), while the output side is associated with the primary side of the electric circuit unit 700. The corona current measurement circuit 730 includes a first operational amplifier 731, an A/D converter 732, a light emitting unit 733, a light receiving unit 734, a second operational amplifier 735 and a D/A converter 736.

The two input terminals of the first operational amplifier 731 are each connected to the lines 761 and 762 while the output terminal is connected to the A/D converter 732. The first operational amplifier 731 amplifies the difference in potential between the lines 761 and 762 to output to the A/D converter 732. The difference in potential between the lines 761 and 762 defines a difference in potential between both the sides of the shunt resistance 230 (FIG. 3) having a known resistance value, and correlates with the current value of the current flowing through the signal line 223 (FIG. 3). In other words, the first operational amplifier 731 amplifies an analog voltage signal indicating the current value of the current flowing through the signal line 223 (FIG. 3) to output to the A/D converter 732. The A/D converter 732 is connected to the first operational amplifier 731 and the light emitting unit 733, and converts the analog signal outputted from the first operational amplifier 731 to a digital signal to output to the light emitting unit 733.

The light emitting unit 733 includes an LED, and is connected to the A/D converter 732 and the secondary-side ground SGL. The light emitting unit 733 converts a digital voltage signal outputted from the A/D converter 732 to a light signal. The light receiving unit 734 includes a photo diode, and is connected to the second operational amplifier 735 and the primary-side ground PGL. The light receiving unit 734 converts the photo signal outputted from the light emitting unit 733 to a current signal to output to the second operational amplifier 735. In this manner, the light emitting unit 733 and the light receiving unit 734 are isolated from one another electrically and physically, and signal transmission therebetween is performed by light.

The second operational amplifier 735 is connected to the light receiving unit 734 and the D/A converter 736, and includes a current-voltage conversion circuit. The second operational amplifier 735 converts the current signal outputted from the light receiving unit 734 to a voltage signal to output to the D/A converter 736. The D/A converter 736 is connected to the second operational amplifier 735 and the line 763, and converts a digital signal outputted from the second operational amplifier 735 to an analog signal to output to the sensor control unit 600 (FIG. 3) via the line 763. Including the above-described configuration, the corona current measurement circuit 730 is capable of outputting the signal inputted from the signal line 223 on the secondary side to the sensor control unit 600 on the primary side while maintaining isolation between the primary side and the secondary side.

According to the above-described fine particle measurement system 10 of the first embodiment (FIG. 3), among the two current measurement circuits (the corona current measurement circuit 730 and the ion current measurement circuit 740) each connected to the primary side and the secondary side of the isolation transformer 720, the corona current measurement circuit 730 constitutes an isolation amplifier and is physically isolated between the primary side and the secondary side. Therefore, the fine particle measurement system 10 according to the present embodiment is configured such that only the ion current measurement circuit 740 electrically connects the primary-side circuit and the secondary-side circuit, which can prevent the generation of a leakage current from the primary side to the secondary side in areas other than the ion current measurement circuit 740. Preventing the generation of a leakage current in areas other than the ion current measurement circuit 740 can reduce an error between the current value of the compensating current Ic supplied to the secondary side and the current value of the leakage current Iesc in the ion current measurement circuit 740. Therefore, according to the fine particle measurement system 10 of the present embodiment, it is possible to increase the accuracy in detecting the amount of the soot S contained in the exhaust gas.

In addition, according to the fine particle measurement system 10 of the first embodiment, because the corona current measurement circuit 730 converts the signal indicating the current value of the current flowing through the signal line 223 to the light signal after amplifying the signal with the use of the first operational amplifier 731, it is possible to increase the accuracy in detecting the amount of the soot S contained in the exhaust gas. Specially, the signal indicating the current value of current flowing through the signal line 223 is minute, so that an error is likely to be discernible in the signal during transmission of the signal from the light emitting unit 733 to the light receiving unit 734. When the signal including the error is inputted to the sensor control unit 600, an error occurs between the current value of the input current Iin supplied to the fine particle sensor 100 and the desired current value, so that an error occurs in the calculated leakage current Iesc as shown in the above-described Equation (2) to decrease the accuracy in detecting the amount of the fine particles contained in the exhaust gas. According to the fine particle measurement system 10 of the present embodiment, because the signal indicating the current value of the current flowing through the signal line 223 is converted to the light signal after being amplified, an error is unlikely to be included in the signal during transmission of the signal from the light emitting unit 733 to the light receiving unit 734. Therefore, according to the fine particle measurement system 10 of the present embodiment, it is possible to increase the accuracy in detecting the amount of the soot S contained in the exhaust gas.

B. Modified Embodiments

The above is not intended to be exhaustive or to limit the present invention to the above-described embodiment, and the present invention can be carried out in various embodiments without departing from the spirit and scope of the claims appended hereto. For example, the following modifications are also possible.

B-1. Modified Embodiment 1

The corona current measurement circuit 730 according to the first embodiment of the present invention (FIG. 4) is configured as an optical coupling type isolation amplifier that transmits signals by light between the light emitting unit 733 and the light receiving unit 734. However, the corona current measurement circuit 730 is not limited to an optical coupling type isolation amplifier as long as the corona current measurement circuit 730 is isolated between the input side and the output side, and is capable of transmitting information from the input side to the output side via an insulating unit. For example, the corona current measurement circuit 730 may be a magnetic coupling type isolation amplifier that transmits signals magnetically, or may be a capacity coupling type isolation amplifier using a coupling capacitor. The use of an optical coupling type isolation amplifier is more preferred in that it has excellent noise resistance and causes less leakage as the corona current measurement circuit 730.

B-2. Modified Embodiment 2

The configuration of the fine particle measurement system 10 described as the first embodiment of the present invention is an example, and the present invention can be achieved by other configurations. For example, the fine particle measurement system 10 need not include the second electrode 132. In addition, the fine particle measurement system 10 may be configured such that the ion generation unit 110 is not disposed inside of the fine particle sensor 100, but the ion generation unit 110 and the fine particle sensor 100 are separately constructed. In addition, the ion generation unit 110 need not be disposed adjacent to the exhaust gas charging unit 120, and may be disposed inside of the exhaust gas charging unit 120.

B-3. Modified Embodiment 3

While the sensor control unit 600 according to the present embodiment controls the discharge voltage control circuit 711 so that the current value of the input current Iin assumes a desired current value in accordance with the signal Sdc+trp outputted from the corona current measurement circuit 730, the configuration of the sensor control unit 600 is not limited thereto. For example, the sensor control unit 600 may be configured to control the discharge voltage control circuit 711 with the use of the signal Sesc outputted from the ion current measurement circuit 740 in addition to the signal Sdc+trp outputted from the corona current measurement circuit 730. The signal Sdc+trp indicates the current value of the current (Idc+Itrp), and the signal Sesc indicates the current value of the current (Iesc). Thus, as shown in the above-described Equation (1), the sensor control unit 600 is capable of further increasing the accuracy in detecting the current value of the input current Iin by using these two signals.

B-4. Modified Embodiment 4

While the fine particle measurement system 10 according to the first embodiment is configured such that the cations are generated between the first electrode 112 and the partition wall 42 by corona discharge, the fine particle measurement system 10 may be configured such that anions are generated by corona discharge. For example, by changing the positive and negative destinations of the first electrode 112 and the partition wall 42, anions can be generated between the first electrode 112 and the partition wall 42.

This application is based on Japanese Patent Application No. 2013-096702 filed May 2, 2013, the disclosure of which is incorporated herein by reference in its entirety.

What is claimed is:

1. A fine particle measurement system comprising:
an ion generating unit configured to generate ions by corona discharge, and a charging chamber configured to charge at least a part of fine particles present in a gas with said ions;
a trapping unit in communication with the charging chamber, and configured to trap at least a part of the generated ions that do not electrically charge the fine particles;
an isolation transformer configured to transform a voltage used for generating the corona discharge, the isolation transformer comprising a secondary side connected to the ion generating unit;
a primary-side power supply circuit connected to a primary side of the isolation transformer, and capable of changing a voltage supplied to the isolation transformer;
a control circuit connected to the primary-side power supply circuit, and configured to control the primary-side power supply circuit so as to adjust a current supplied to the ion generating unit;
a first current measurement circuit connected to each of a secondary-side reference potential line of a secondary side of the isolation transformer, the trapping unit and the control circuit, and configured to transmit to the control circuit a first signal indicating a first current that flows from the trapping unit toward the secondary-side reference potential line; and
a second current measurement circuit connected to each of a primary-side reference potential line of a primary side of the isolation transformer, the secondary-side reference potential line and the control circuit, and configured to transmit to the control circuit a second signal indicating a second current that is obtained based on a potential difference between the primary-side reference potential line and the secondary-side reference potential line, the second current corresponding to an amount of ions that are not trapped by the trapping unit,
wherein the control circuit is configured to adjust the current supplied to the ion generating unit to a desired value in accordance with the first current, and to measure the amount of the fine particles in the gas in accordance with the second current, and
wherein the first current measurement circuit comprises an isolation amplifier and is configured to amplify the first signal via the isolation amplifier to transmit the first signal to the control circuit.

2. The fine particle measurement system as claimed in claim 1, wherein the gas comprises an exhaust gas exhausted from an internal combustion engine, and wherein the charging chamber is disposed in an exhaust pipe through which the exhaust gas passes.

* * * * *